US00PP28648P3

(12) United States Plant Patent
Beekenkamp

(10) Patent No.: US PP28,648 P3
(45) Date of Patent: Nov. 14, 2017

(54) ***BEGONIA* PLANT NAMED 'BKPBELLV'**

(50) Latin Name: *Begonia boliviensis*
Varietal Denomination: BKPBELLV

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 39 days.

(21) Appl. No.: 14/756,924

(22) Filed: Oct. 30, 2015

(65) Prior Publication Data

US 2017/0127593 P1 May 4, 2017

(51) Int. Cl.
*A01H 5/02* (2006.01)

(52) U.S. Cl.
USPC ..... Plt./347

(58) Field of Classification Search
USPC ..... Plt./347
See application file for complete search history.

*Primary Examiner* — Keith Robinson
(74) *Attorney, Agent, or Firm* — C. A. Whealy

(57) ABSTRACT

A new and distinct cultivar of *Begonia* plant named 'BKPBELLV', characterized by its upright to broadly outwardly spreading and mounded plant habit; freely branching habit; dark green-colored leaves; uniform and freely flowering habit; bright orange-colored flowers; and good garden performance.

2 Drawing Sheets

Botanical designation: *Begonia boliviensis*.
Cultivar denomination: 'BKPBELLV'.

BACKGROUND OF THE INVENTION

The present invention relates to a new and distinct cultivar of *Begonia* plant, botanically known as *Begonia boliviensis* and hereinafter referred to by the name 'BKPBELLV'.

The new *Begonia* plant is a product of a planned breeding program conducted by the Inventor in Maasdijk, The Netherlands. The objective of the breeding program was to develop new compact, freely branching and freely flowering *Begonia* plants with attractive flowers.

The new *Begonia* plant originated from a cross-pollination made by the Inventor in November, 2010 of a proprietary selection of *Begonia boliviensis* identified as code number H10-263-07, not patented, as the female, or seed, parent with a proprietary selection of *Begonia boliviensis* identified as code number 10-000-26, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in May, 2011.

Asexual reproduction of the new *Begonia* plant by vegetative tip cuttings in a controlled greenhouse environment in Maasdijk, The Netherlands since August, 2011 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBELLV'. These characteristics in combination distinguish 'BKPBELLV' as a new and distinct *Begonia* plant:

1. Upright to broadly outwardly spreading and mounded plant habit.
2. Freely branching habit.
3. Dark green-colored leaves.
4. Uniform and freely flowering habit.
5. Bright orange-colored flowers.
6. Good garden performance.

Plants of the new *Begonia* can be compared to plants of the female parent selection. Plants of the new *Begonia* differ primarily from plants of the female parent selection in the following characteristics:

1. Plants of the new *Begonia* have smaller flowers than plants of the female parent selection.
2. Plants of the new *Begonia* have bright orange-colored flowers whereas plants of the female parent selection have red-colored flowers.
3. Flower tepals and tepaloids of plants of the new *Begonia* have pointed apices whereas flower tepals and tepaloids of plants of the female parent selection have rounded apices.

Plants of the new *Begonia* can be compared to plants of the male parent selection. Plants of the new *Begonia* differ primarily from plants of the male parent selection in the following characteristics:

1. Plants of the new *Begonia* are more compact than and not as trailing as plants of the male parent selection.
2. Plants of the new *Begonia* have smaller flowers than plants of the male parent selection.

3. Plants of the new *Begonia* have bright orange-colored flowers whereas plants of the male parent selection have red-colored flowers.

Plants of the new *Begonia* can be compared to plants of the *Begonia boliviensis* 'BKPBEBVSL', disclosed in U.S. Plant Pat. No. 25,620. In side-by-side comparisons conducted in Maasdijk, The Netherlands, plants of the new *Begonia* differ from plants of 'BKPBEBVSL' in the following characteristics:

1. Plants of the new *Begonia* are more compact than and not as trailing as plants of 'BKPBEBVSL'.
2. Plants of the new *Begonia* have smaller flowers than plants of 'BKPBEBVSL'.
3. Plants of the new *Begonia* have bright orange-colored flowers whereas plants of 'BKPBEBVSL' have orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBELLV' grown in a container.

The photograph on the second sheet are close-up views of upper and lower surfaces of typical flowers and leaves of 'BKPBELLV' and at the center of the photograph is a close-up view of typical flower buds and opening flowers with pedicels.

DETAILED BOTANICAL DESCRIPTION

Plants used for the aforementioned photographs and following observations and measurements were grown in 12-cm containers during the late summer in a glass-covered greenhouse in Maasdijk, The Netherlands. During the production of the plants, day temperatures ranged from 19° to 20° C., night temperatures ranged from 18° to 19° C. and light levels averaged 6,000 lux. Plants were ten weeks old when the photographs and the description were taken. In the following description, color references are made to The Royal Horticultural Society Colour Chart, 2015 Edition, except where general terms of ordinary dictionary significance are used.

Botanical classification: *Begonia boliviensis* 'BKPBELLV'.

Parentage:

*Female, or seed, parent.*—Proprietary selection of *Begonia boliviensis* identified as code number H10-263-07, not patented.

*Male, or pollen, parent.*—Proprietary selection of *Begonia boliviensis* identified as code number 10-000-26, not patented.

Propagation:

*Type.*—By vegetative tip cuttings.

*Time to initiate roots.*—About 20 days at temperatures about 25° C.

*Time to produce a rooted young plant.*—About 35 to 36 days at temperatures about 21° C. to 23° C.

*Root description.*—Fine, fibrous; typically light brown in color, actual color of the roots is dependent on substrate composition, water quality, fertilizer type and formulation, substrate temperature and physiological age of roots; plants of the new *Begonia* have not been observed to form tubers.

*Rooting habit.*—Moderate freely branching; medium density.

Plant description:

*Plant and growth habit.*—Upright to broadly outwardly spreading and mounded plant habit; plant shape roughly flattened globular; freely branching habit with about 20 basal and lateral branches developing per plant; low vigor and slow growth rate.

*Plant height.*—About 11.3 cm.

*Plant width.*—About 22.1 cm.

*Lateral branch description.*—Length: About 4 cm. Diameter: About 3 mm. Internode length: About 7 mm. Strength: Weak, bending with the weight of the leaves and flowers. Aspect: About 30° from the vertical and main stem axis. Texture: Pubescent. Luster: Slightly glossy. Color, developing: Close to 152A heavily tinged with close to 177C to 177D. Color, fully developed: Close to 185A to 185B.

*Leaf description.*—Arrangement: Alternate (distichous), simple. Length: About 5.5 cm. Width: About 2.1 cm. Shape: Unequally ovate. Apex: Acute. Base: Unequal, hastate; lobes not imbricate. Margin: Dentate to serrate. Texture, upper and lower surfaces: Sparsely pubescent; velvety. Luster, upper surface: Moderately glossy. Luster, lower surface: Slightly glossy. Venation pattern: Laciniate. Color: Developing leaves, upper surface: Close to darker than between 139A and N189A. Developing leaves, lower surface: Close to 187D. Fully expanded leaves, upper surface: Darker than 147A; venation, close to 143A. Fully expanded leaves, lower surface: Close to 182A to 182B; venation, close to 146B. Petioles: Length: About 1.4 cm. Diameter: About 1.5 mm. Texture, upper and lower surfaces: Pubescent. Luster, upper and lower surfaces: Glossy. Color, upper surface: Close to 179B; distally, close to 185A. Color, lower surface: Close to 179B. Stipules: Quantity per leaf: Two. Length: About 2 mm. Width: About 1.5 mm. Shape: Deltoid. Apex: Acute. Base: Broadly cuneate. Margins: Entire. Color, upper and lower surfaces: Close to N155B; towards the base, tinged with close to 60A to 60B.

Flower description:

*Flowering habit.*—Rotate semi-double male flowers and rotate single female flowers; flowers either singly or arranged in axillary cymes; freely flowering habit with about two to three flowers per cyme and about 200 flowers developing per plant; flowers face upright to outwardly.

*Fragrance.*—None detected.

*Natural flowering season.*—Plants begin flowering about 44 days after planting; long flowering period, plants flower freely and continuously from spring into the autumn in The Netherlands.

*Postproduction longevity.*—Individual flowers last about one week on the plant; flowers not persistent; plants maintain good substance for about two to three months.

*Inflorescence height.*—About 7 cm.

*Inflorescence diameter.*—About 4.5 cm.

*Flower buds.*—Length: About 1.4 cm. Diameter: About 5 mm to 10 mm. Shape: Broadly obovate to flabellate; flattened. Color: Close to 32A.

*Male flowers.*—Diameter: About 3 cm. Depth: About 1.9 cm. Tepals: Quantity per flower and arrangement: Four in opposite pairs. Length, pair of broader tepals: About 1.9 cm. Width, pair of broader tepals: About 1.3 cm. Length, pair of narrower tepals: About 2 cm. Width, pair of narrower tepals: About 8 mm. Shape, pair of broader tepals: Ovate. Shape, pair of narrower tepals: Narrowly ovate. Apex, all tepals: Acute to bluntly acute. Margin, all tepals: Entire. Texture, upper surface: Smooth, glabrous; moderately velvety. Texture, lower surface: Smooth, glabrous; slightly velvety. Luster, upper surface: Matte. Luster, lower surface: Moderately glossy. Color: When opening, upper surface: Close to N30B. When opening, lower surface: Close to 33A to 33B. Fully opened, upper surface: Close to N30B; color does not fade with development. Fully opened, lower surface: Close to 32A; color does not fade with development.

*Tepaloids.*—Present on male flowers only. Quantity per flower and arrangement: About three in a single whorl. Length: About 1 cm to 1.6 cm. Width: About 2 mm to 4 mm. Shape: Lanceolate. Apex: Rounded. Margin: Entire. Texture, upper and lower surfaces: Smooth, glabrous; moderately velvety. Luster, upper and lower surfaces: Matte. Color: When opening, upper and lower surfaces: Close to N30B. Fully opened, upper surface: Close to 33A to 33B; color does not fade with development. Fully opened, lower surface: Close to N30B; color does not fade with development.

*Female flowers.*—Diameter: About 1.9 cm. Depth: About 1.4 cm. Tepals: Quantity per flower and arrangement: Five, arranged in a single whorl. Length: About 1.5 cm. Width: About 7.5 mm. Shape: Ovate to narrowly ovate. Apex: Acute to bluntly acute. Margin: Entire. Texture, upper surface: Smooth, glabrous; moderately velvety. Texture, lower surface: Smooth, glabrous; slightly velvety. Luster, upper surface: Matte. Luster, lower surface: Moderately glossy. Color: When opening and fully opened, upper surface: Close to N30B; color does not fade with development. When opening and fully opened, lower surface: Close to 32A; color does not fade with development. Tepaloids: None observed on female flowers.

*Peduncles, male and female flowers.*—Length: About 3.1 cm. Diameter: About 1.5 mm. Angle: About 30° from lateral branch axis. Strength: Moderately strong; flexible and bending with the weight of the flowers. Texture: Very sparsely pubescent. Luster: Moderately glossy. Color: Close to 144B to 144C; towards the base, tinged with close to 185B.

*Pedicels, male and female flowers.*—Length: About 2.3 cm. Diameter: About 1 mm. Angle: About 30° to 40° from the peduncle axis. Strength: Weak to moderately strong; flexible, bending with the weight of the flowers. Texture: Smooth, glabrous. Luster: Moderately glossy. Color: Close to 31A; towards the base, closer to 145C.

*Flower bracts.*—Quantity per flower: Two. Length: About 4 mm. Width: About 4 mm. Shape: Broadly ovate. Margin: Entire. Texture, upper and lower surfaces: Smooth, glabrous; velvety. Luster, upper and lower surfaces: Moderately glossy. Color, upper and lower surfaces: Close to 144C; towards the margins, close to 185B.

*Reproductive organs.*—Androecium: Present only on male flowers. Stamen quantity per flower: About 40. Filament length: About 2 mm. Filament color: Close to 13A. Anther length: About 1 mm. Anther shape: Ovate. Anther color: Close to 14A. Amount of pollen: Moderate. Pollen color: Close to 4D. Gynoecium: Present only on female flowers. Quantity per flower: Six, fused in pairs. Pistil length: About 4 mm. Stigma shape: Spiral. Stigma color: Close to 17B. Style length: About 1 mm. Style color: Close to 23A. Ovary color: Close to 144C strongly tinged with close to 178A to 178B. Seeds and fruits: Seed and fruit development have not been observed on plants of the new *Begonia*.

Disease & pest resistance: Resistance to pathogens and pests common to *Begonia* plants has not been observed on plants of the new *Begonia*.

Garden performance & temperature tolerance: Plants of the new *Begonia* have been observed to have good garden performance, to tolerate high temperatures of about 35° C. and to be hardy to USDA Hardiness Zone 10.

It is claimed:

1. A new and distinct *Begonia* plant named 'BKPBELLV' as illustrated and described.

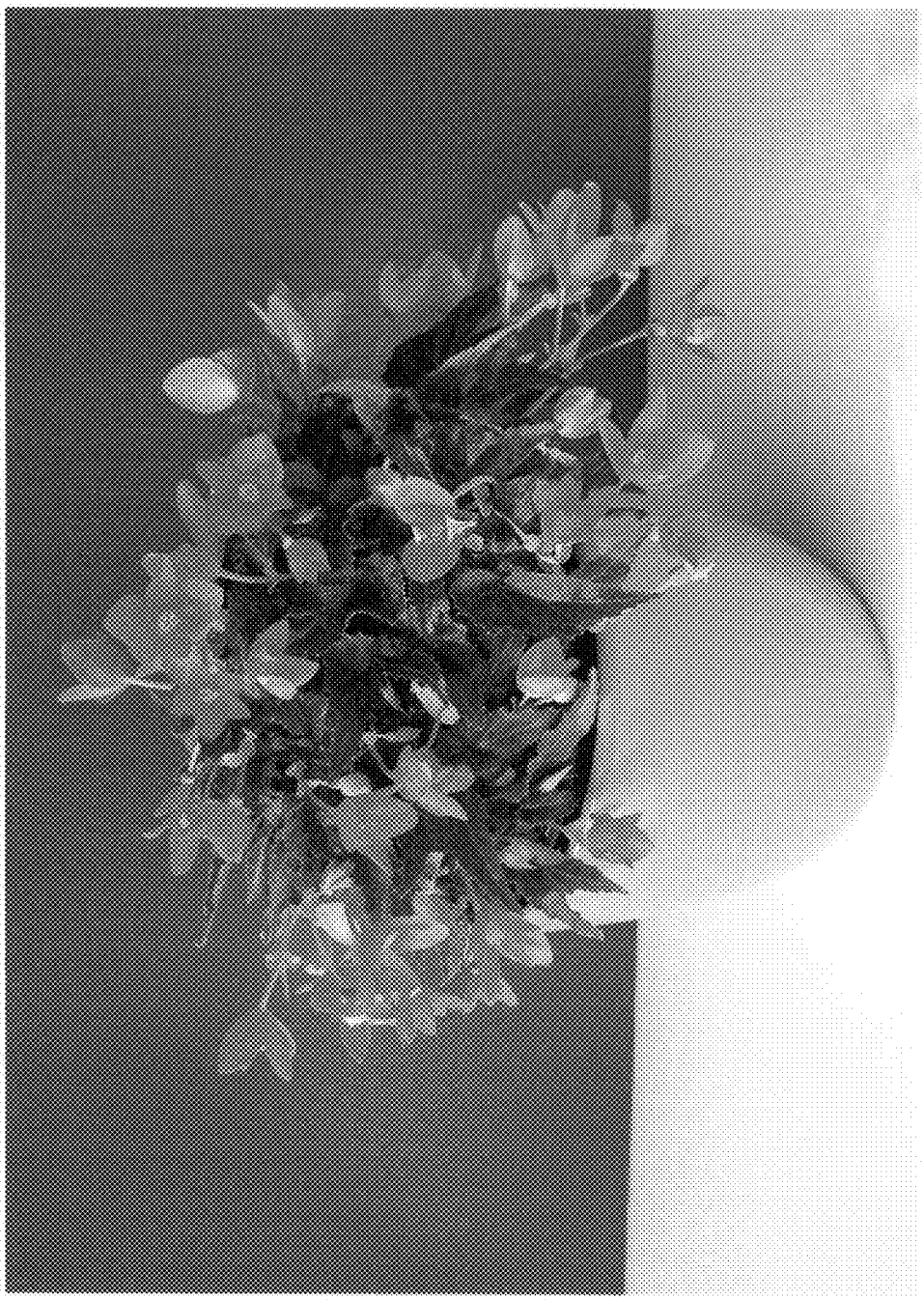

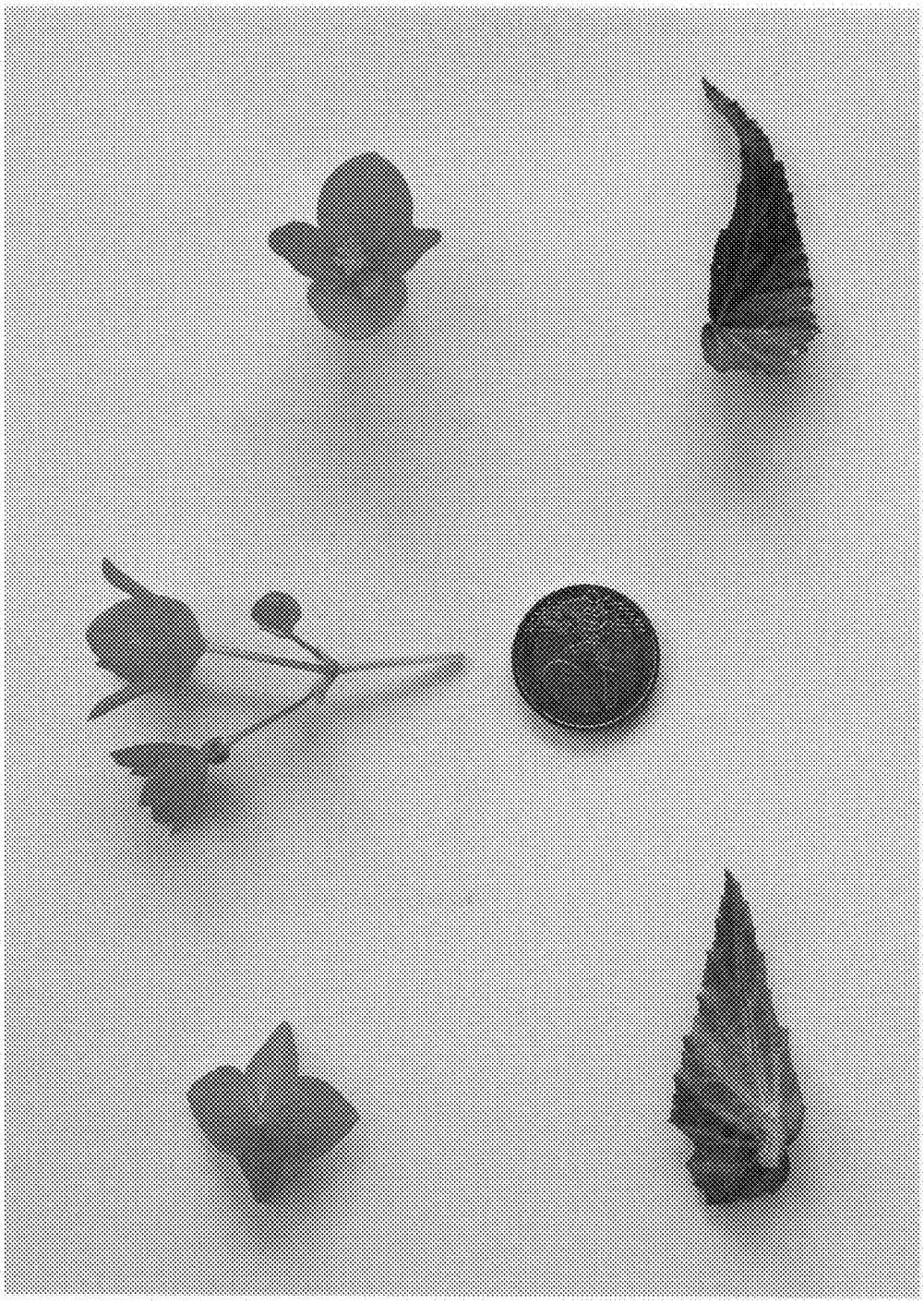

* * * * *